United States Patent
Heukensfeldt Jansen

[19]

[11] Patent Number: 5,936,248
[45] Date of Patent: Aug. 10, 1999

[54] MULTIPLE ENERGY SCINTILLATION CAMERA SPATIAL CORRECTION METHOD AND APPARATUS

[75] Inventor: Floribertus P. M. Heukensfeldt Jansen, Brookfield, Wis.

[73] Assignee: General Electric Company, Milwaukee, Wis.

[21] Appl. No.: 09/002,200

[22] Filed: Dec. 31, 1997

[51] Int. Cl.$^6$ .................................................. G01T 1/164
[52] U.S. Cl. ................................. 250/363.07; 250/363.03
[58] Field of Search ........................... 250/363.03, 363.07

[56] References Cited

U.S. PATENT DOCUMENTS

5,345,082  9/1994  Engdahl et al. ................... 250/363.07

*Primary Examiner*—Constantine Hannaher
*Assistant Examiner*—Andrew Israel
*Attorney, Agent, or Firm*—Quarles & Brady; Christian G. Cabou; Phyllis Y. Price

[57] ABSTRACT

A method for use with a scintillation camera which detects radiation events having energies within two different energy ranges and distorts spatial coordinates of detected events in the two ranges differently, a spatial coordinate set is determined for each event, each coordinate set is adjusted using a first set of predetermined correction factors calculated to eliminate distortion in events within a first of the energy ranges yielding first corrected coordinate sets corresponding to events within the first energy range and adjusted sets corresponding to events within the second energy range, adjusted sets are further adjusted using a second set of predetermined correction factors calculated to eliminate distortion in the adjusted sets yielding corrected second sets, the first and second sets are then used to generate first and second images, respectively.

9 Claims, 7 Drawing Sheets

MULTIPLE ENERGY SCINTILLATION CAMERA SPATIAL CORRECTION METHOD AND APPARATUS

BACKGROUND OF THE INVENTION

The present invention relates to gamma cameras and more specifically to a method and apparatus for use with a scintillation camera for correcting distortions in images acquired simultaneously at two different energy levels.

In emission imaging, examinations are carried out by injecting a dilution marker comprising a compound labeled with a radiopharmaceutical into the body of a patient to be examined. A radiopharmaceutical is a substance that emits photons at one or more energy levels. By choosing a compound that will accumulate in an organ to be imaged (hereinafter an organ of interest), compound concentration, and hence radiopharmaceutical concentration, can be substantially limited to an organ. Typically a radiopharmaceutical that emits photons at approximately a single known energy level is chosen. An energy range which approximates the known energy level will be referred to as the marker range.

While moving through a patient's blood stream the marker, including the radiopharmaceutical, becomes concentrated in the organ of interest. By measuring the number of photons emitted from the organ of interest which are within the marker range, organ characteristics, including irregularities, can be identified.

To measure the number of emitted photons, one or more planar gamma cameras are used. After a marker has become concentrated within an organ of interest, a camera is positioned at an imaging angle with respect to the organ of interest such that the organ is positioned within the camera's field of view (FOV). The camera is designed to detect photons traveling along preferred paths within the FOV.

A gamma camera consists of a collimator, a scintillation crystal, a plurality of photomultiplier tubes (PMTs) and a camera processor. The collimator typically includes a rectangular lead block having a width dimension and a length dimension which together define the FOV. The collimator block forms tiny holes which pass therethrough defining preferred photon paths which are unidirectional and perpendicular to the length of the collimator. The collimator blocks emissions toward the crystal along non-preferred paths.

The scintillation crystal is positioned adjacent the collimator on a side opposite the FOV and has an impact surface and an oppositely facing emitter surface. The impact surface defines a two dimensional imaging area A having a length L and a width W. Photons which pass through the collimator impact and are absorbed by the impact surface at impact points, each point having actual impact coordinates X and Y along length L and width W dimensions. The crystal emitter surface emits light from an emitter point adjacent the impact point each time a photon is absorbed. The amount of light emitted depends on the absorbed photon's energy level.

The PMTs are arranged in a two dimensional array which is positioned adjacent the emitter surface. Light emitted by the crystal is detected by the PMTs. Each PMT which detects light generates an analog intensity signal which is proportional to the amount of light detected. When a single photon is absorbed by the crystal, the emitted light is typically absorbed by several different PMTs such that several PMTs generate intensity signals simultaneously. For the purposes of this explanation all intensity signals caused by a single photon will be collectively referred to as a signal set.

The processor receives each signal set and performs a plurality of calculations on each signal set to determine two characteristics of the corresponding photon. First, the processor combines the intensity signals of each signal set to identify the energy level Z of a corresponding photon. Photons having energies within the marker range will be referred to as events. Only signals corresponding to events are used for imaging. Second, the processor performs a series of calculations in an effort to determine precise impact coordinates X and Y of each event. Hereinafter, actual impact coordinates will be referred to as X and Y while calculated coordinates will be referred to as Xc and Yc. Once coordinates X and Y of all events have been identified, the processor uses the coordinates of many events (typically millions) to create an image of the organ of interest.

Unfortunately, images formed from calculated impact coordinates Xc and Yc are often spatially distorted. Spatial distortion occurs when calculated coordinates Xc and Yc diverge from actual event coordinates X and Y. This distortion occurs because calculated coordinates Xc and Yc are dependent upon, and are a function of, the spatial relationship between a photon's impact point and adjacent PMTs. The effect of this type of distortion is that the number of events perceived in the central areas of many PMTs is greater than the actual number of events which occur in those areas while the number of events perceived in edge areas of many PMTs is less than the actual number of events which occur. This incorrect event concentration causes images generated using the event information to have a non-uniform appearance and therefore limits their diagnostic usefulness.

To compensate for PMT spatial distortion, the industry has developed spatial coordinate correction methods usually implemented in software. According to these methods, after event coordinates Xc and Yc have been calculated, the coordinates are then shifted as a function of coordinate correction factors to compensate for incorrect event concentrations along both X and Y coordinate axis. The shifts generate modified coordinates Xm and Ym for each photon wherein the modified coordinates are nearly identical to actual coordinates X and Y.

To identify correction factors, a radiation image having a known pattern and known energy such as a grid of parallel lines or points (typically formed using a radio-opaque grid), is directed at a camera. Xc and Yc coordinates are then computed and compared with known coordinates X and Y which correspond to the grid pattern. The comparison yields correction factors which, when applied to calculated coordinates Xc and Yc, generate modified coordinates Xm and Ym which are identical to actual coordinates X and Y.

In medical imaging, it is sometimes desirable to generate two nuclear images simultaneously using first and second radiopharmaceuticals, the first radiopharmaceutical emitting photons at a first energy and the second radiopharmaceutical emitting photons at a second energy different than the first. For example, photons at the first energy might be better suited for identifying scarred tissue while photons at the second energy might be better suited for imaging blood flow or some other biological process or tissue. The quantity of light produced by the crystal upon photon absorption is approximately linearly proportional to an absorbed photons energy. For example, a photon of 511 keV would produce approximately 3.6 times the quantity of light produced by a photon of 140 keV. The processor can identify each photon energy and separate absorbed photons into two different groups, each group including photons at one of the two energy levels. Then, the processor can construct two different images using modified impact coordinates Xm and Ym corresponding to the two different photon groups.

In addition to being dependent on PMT location and construction, spatial coordinate correction factors are also dependent on photon energy. This is because photon energy affects operation of the processor's electronic circuitry in a non-linear fashion. For example, where a photon of 511 keV is absorbed at coordinates X and Y, the processor might generate calculated coordinates Xca ands Yca whereas, where a photon of 140 keV is absorbed at coordinates X and Y, the processor might generate calculated coordinates Xcb and Ycb which are slightly different than coordinates Xca and Yca.

The most obvious solution to correct for non-linearities due to different photon energies is to generate one set of spatial coordinate correction factors for a first energy and a second set of spatial coordinate correction factors for a second energy and then apply the first and second factor sets to calculated impact coordinates corresponding to photons at the first and second energies, respectively. One such method has been described in U.S. Pat. No. 5,345,082 entitled "Scintillation Camera Utilizing Energy Dependent Linearity Correction" which issued on Sep. 6, 1994 which is incorporated herein by reference. According to that patent, during imaging and after a processor detects a photon event, the processor generates energy signal Z corresponding to the event, compares signal Z with energy signal ranges corresponding to different radiopharmaceutical energy levels to identify an energy range including signal Z, computes calculated coordinates Xc and Yc, retrieves a correction factor set corresponding to the energy range, identifies correction factors within the retrieved set which correspond to calculated coordinates Xc and Yc and modifies coordinates Xc and Yc according to the correction factors. This entire process is performed during data acquisition.

While this solution to the energy distortion problem can facilitate distortion correction, this solution cannot be implemented by every gamma camera processor. This is because many camera processors were designed to correct for spatial distortion corresponding to photons at a single energy level and therefore cannot support distortion correction corresponding to events at more than one energy without hardware modifications. In these cases, while processor hardware might be able to separate events into first and second energy ranges, the processor can only modify calculated coordinates according to a single correction factor set corresponding to the first energy range. Thus, while modified coordinates corresponding to events within the first energy range will be correct, modified coordinates corresponding to events within the second energy range will be incorrect and an image formed using the second set of modified coordinates will be will be of lower quality for diagnostic purposes.

In addition, this solution requires an extremely complex and hence expensive processor to perform all processor functions during data acquisition. One way to implement this solution less expensively might be to store sets of acquired data during acquisition for later "off-line" processing. If the position coordinates are reduced to, say 7 or 8 bits as is usual in nuclear medicine imaging, some position information is lost which renders subsequent correction less accurate. This problem is worst for completely uncorrected images where the distortion may be relatively large.

Therefore, it would be advantageous to have a universal method for correcting calculated event coordinates for events at two or more energy levels which could be implemented using essentially any camera processor without modification to existing hardware and without reduction in data accuracy.

BRIEF SUMMARY OF THE INVENTION

The present invention overcomes the limitations discussed above by, for each calculated coordinate corresponding to an event at either a first or a second energy, allowing the processor to adjust coordinates as a function of a first set of correction factors corresponding to the first energy. At that point, coordinates corresponding to events at the first energy which were adjusted are essentially identical to actual event coordinates and therefore can be used to generate an accurate diagnostic image corresponding to events at the first energy.

Next, adjusted coordinates corresponding to events at the second energy are adjusted a second time, this time as a function of a second set of correction factors calculated to eliminate error between the adjusted coordinates and actual event coordinates at the second energy. Coordinates corresponding to events at the second energy which were adjusted this second time are essentially identical to actual event coordinates and therefore can be used to generate an accurate diagnostic image corresponding to events at the second energy. Preferably, this second round of adjustments is performed during a post-acquisition procedure and can be performed by either the camera processor or some other computer linked to the camera processor.

Thus, one object of the invention is to provide a method for correcting calculated event coordinates for photons at more than one energy level in a manner which can be implemented using most gamma camera hardware. To this end, a processor capable of correcting event coordinates corresponding to only a single energy level is employed during acquisition to adjust every event coordinate corresponding to an event at either a first or a second energy as a function of a first correction factor set calculated to eliminate spatial distortion in coordinates corresponding to events at the first energy. Then, adjusted coordinates corresponding to events at the second energy are further adjusted by a second correction factor set calculated to eliminate spatial distortion in adjusted coordinates corresponding to events at the second energy.

Another object is to allow existing camera processors to implement dual-isotope imaging processes despite hardware limitations. The inventive method can be implemented in software without hardware modifications.

One other object is to use a processor which can only correct spatial distortion using a single set of correction factors at a time to process events having two different energies and requiring different sets of correction factors without losing imaging precision due to memory storage. For example, where a processor can provide 12-bit words indicating event coordinates and a memory only allows 8-bit words to be stored, precision is reduced by 4-bits if data must be stored prior to processing. With the present invention, a large portion of total coordinate correction for events at the second energy level is performed using the first correction factor set and thus, after the first correction, only very little precision is sacrificed by storing modified coordinates as opposed to calculated coordinates.

Other objects, advantages and aspects of the invention will become apparent from the following description. In the description, reference is made to the accompanying drawings which form a part hereof, and in which there is shown a preferred embodiment of the invention. Such embodiment does not necessarily represent the full scope of the invention and reference is made therefor, to the claims herein for interpreting the scope of the invention.

DETAILED DESCRIPTION OF THE INVENTION

A. Theory

Figure 1:
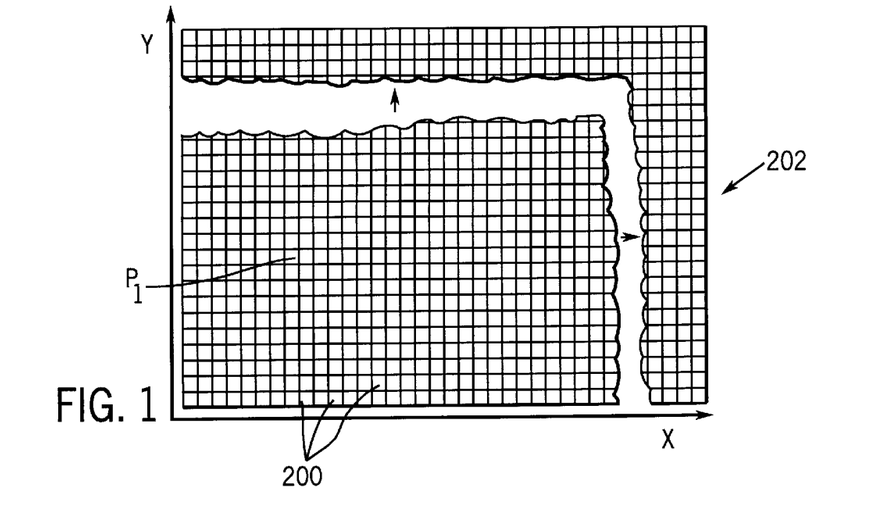
FIG. 1 is a schematic of a pixellated image.

Referring to FIG. 1, an image generated using a photon camera, like a television image, includes a plurality of pixels collectively referred to by numeral 200, which are arranged in a two dimensional array 202 along X and Y image coordinates. Image contrast is generated by varying the intensity of each pixel 200 such that, from a distance (e.g. a few inches), different sections of the image can be identified.

When data corresponding to two images are to be generated simultaneously using radiopharmaceuticals which emit photons at two different energies, energy dependent spatial distortion occurs along both X and Y image dimensions thereby causing errors in both images. For the purposes of this explanation, detected photons at either a first or second energy level will be referred to as events, events at the first energy will be referred to collectively as a first event set and events at the second energy will be referred to collectively as a second event set.

According to the present invention, despite the fact that spatial distortion is energy dependent, coordinates of every event are corrected using a first correction factor set Z1 calculated to eliminate spatial distortion in events at the first energy. This first correction step is preferably performed during data acquisition and yields a first corrected set of coordinates corresponding to the first event set and an adjusted set of coordinates corresponding to the second event set. The adjusted set retains some residual distortion.

Next, a second correction factor set is applied to the adjusted set to yield a second corrected set of coordinates which do not have residual spatial distortion. The first and second corrected sets of coordinates can then be used to generate first and second images, respectively. Preferably, the second set of correction factors is applied post-acquisition so that a camera processor is not burdened.

B. Hardware

Figure 2:
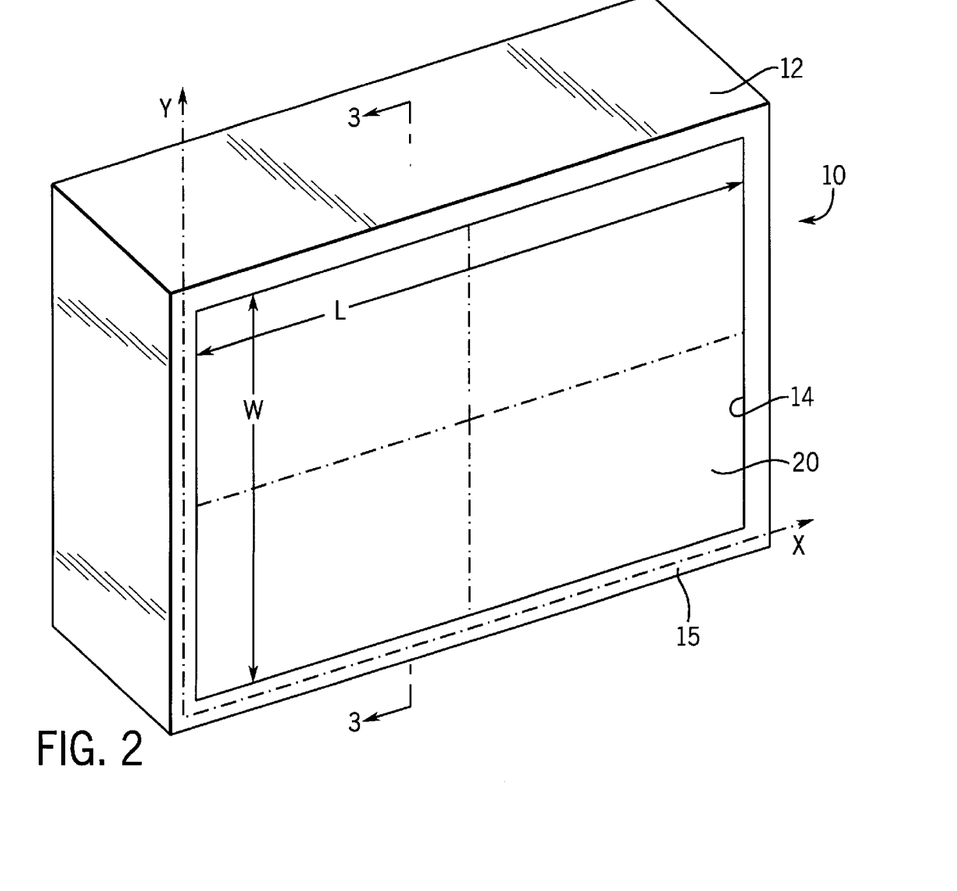
FIG. 2 is a perspective view of a gamma camera.
Figure 3:
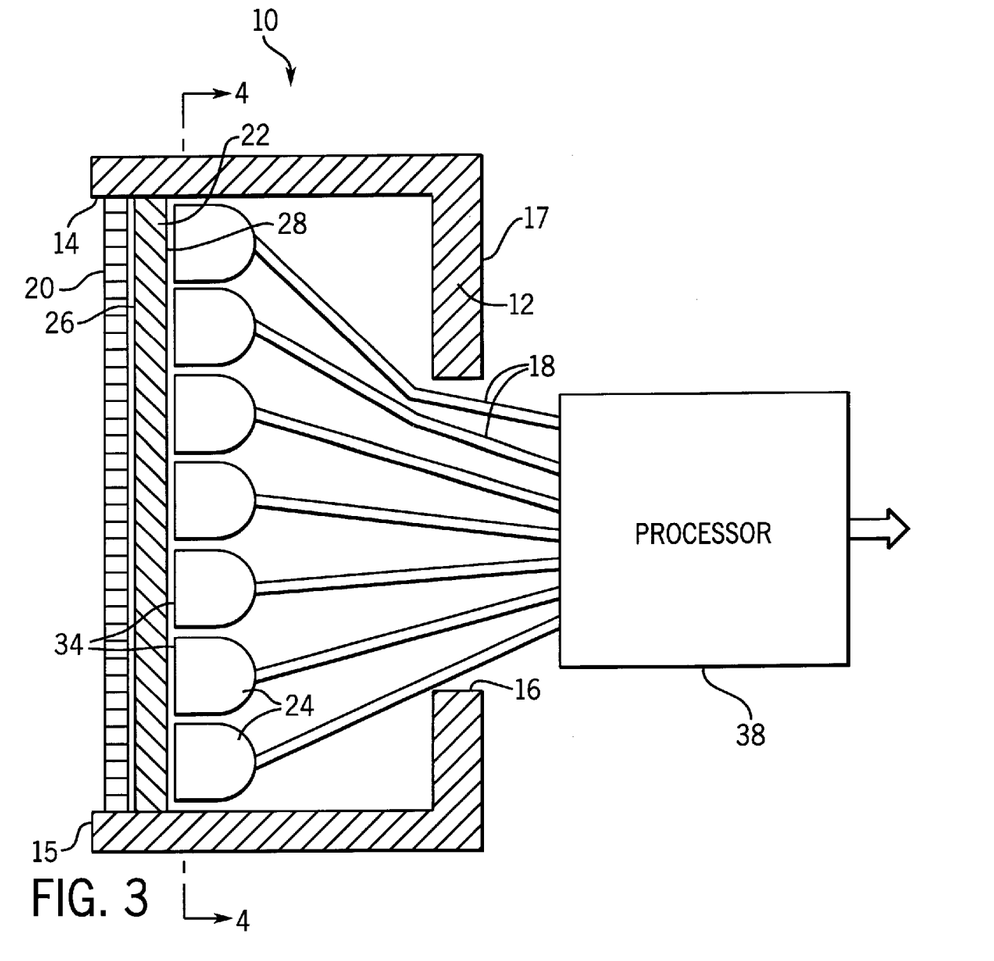
FIG. 3 is a partial cross-sectional view of the gamma camera of FIG. 2 taken along the line 3—3.

Referring now to FIGS. 1 through 10, wherein like referenced characters represent corresponding elements throughout the several views, and more specifically, referring to FIG. 2, therein is illustrated a single gamma camera detector 10 which includes a gamma attenuating boot 12 and a collimator 20. Referring also to FIG. 3, boot 12 defines a collimator receiving opening 14 at a first side 15 and defines an opening 16 in an opposite facing back surface 17 to allow data buses collectively referred to by numeral 18 to pass therethrough.

A plurality of detector elements are housed inside boot 12 including collimator 20, a scintillation crystal 22 and a plurality of photomultiplier tubes (PMTs) collectively referred to by numeral 24.

Collimator 20 is planar having a length L and a width W sized such that, when mounted within opening 14, collimator 20 closes opening 14. Collimator 20 forms a plurality of apertures which define preferred photon flight paths passing through collimator 20, perpendicular to both of the collimator length and width. Thus, any photons passing through collimator 20 are directed directly at crystal 22.

Referring still to FIG. 3, crystal 22 is adjacent collimator 20, is planar and has dimensions (not illustrated) which are essentially identical to length L and width W dimensions. Crystal 22 includes oppositely facing impact and emitter surfaces 26, 28, respectively. Crystal 22 is mounted inside boot 12 within impact surface 26 facing collimator 20.

Figure 4:
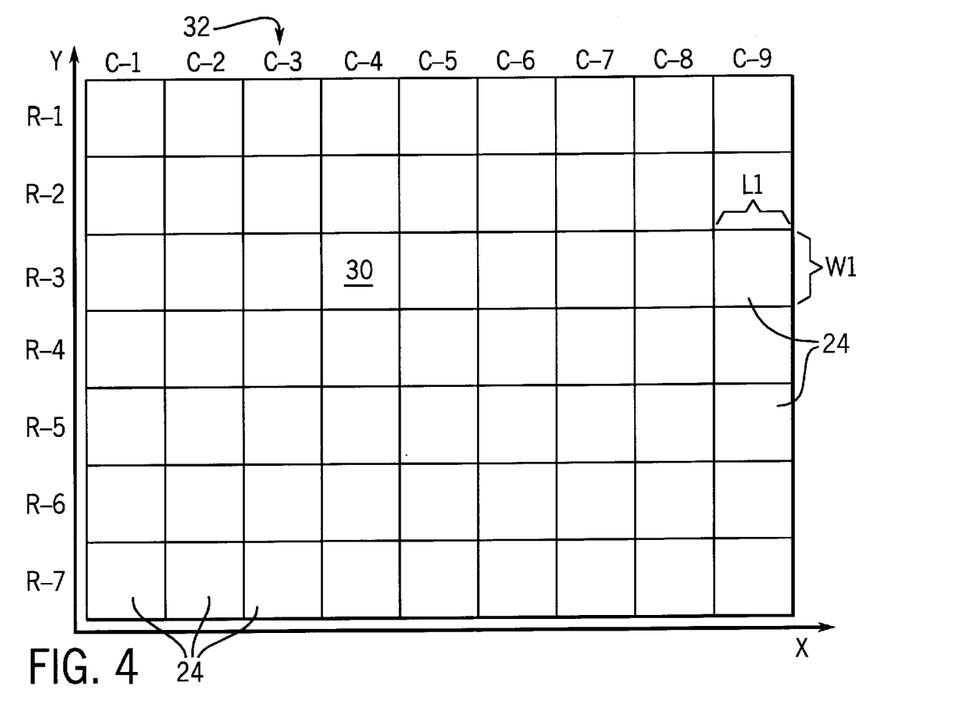
FIG. 4 is a partial cross-sectional view taken along the line of 4—4 of FIG. 3.

Referring now to FIGS. 3 and 4, PMTs 24 are arranged to form a two-dimensional PMT array 32 including PMT rows R–1 through R–7 and columns C–1 through C–9. Array 32 is mounted inside boot 12 such that PMT detecting surfaces referred to by numeral 34 face a surface 28 of crystal 22. Each PMT 24 is linked via a unique emitter bus cable 18 to processor 38. Camera 10 is mounted in a location with a respect to an imaging area.

In operation, with first and second markers which includes first and second radiopharmaceuticals that emit photons at first and second energy levels accumulated within an organ of interest (i.e. an organ to be imaged) and with the organ position within the imaging area, photons emitted by each of the first and second radiopharmaceuticals radiate from the organ in all directions. Photons directed at collimator 20 pass through collimator 20 and impact surface 26. Each photon passing through collimator 20 impacts surface 26 at an impact point and is detected by crystal 22. When a photon is detected by crystal 22 at an impact point, crystal 22 emits light from an emitter point on emitter surface 28 which is adjacent the photon's impact point. Light emitted by crystal 22 is detected by detectors 24, each detector 24 generating an intensity signal which is approximately proportional to the quantum of light detected (i.e., is related to the energy of the photons). Thus, photons which radiate from the first radiopharmaceutical generate intensity signals which have a different intensity than intensity signals caused by photons which radiate from the second radiopharmaceutical.

For every absorbed photon, virtually every PMT in array 32 generates an intensity signal. Referring to FIG. 3, bus cables 18 provide intensity signals from PMTs 24 to processor 38. Processor 38 receives all intensity signals corresponding to each absorbed photon and performs a plurality of calculations to determine coordinates Xc and Yc on the impact surface at which a photon impact point occurred.

Prior to generating images corresponding to the intensity signals, processor 38 first separates event impact coordinates Xc and Yc into first and second groups corresponding to photons at the first and second energy levels, respectively. When coordinates Xc and Yc of all photons have been identified and separated into the first and second groups as a function of energy levels, the processor uses coordinates Xc and Yc to create two separate images of the organ of interest. The first image is created using coordinates Xc and Yc from the first group while the second image is generated using coordinates Xc and Yc from the second group.

In addition, prior to generating the first and second images, processor 38 first performs a plurality of different coordinates correction steps in order to correct coordinates Xc and Yc for errors which occur during processing. As described in more detail above, the correction factors depend on photon energy level. In other words, coordinates Xc and Yc corresponding to photons at the first energy level have different correction factors than coordinates Xc and Yc corresponding to photons at the second energy level.

C. Generating Correction Factor Sets

Figure 5:
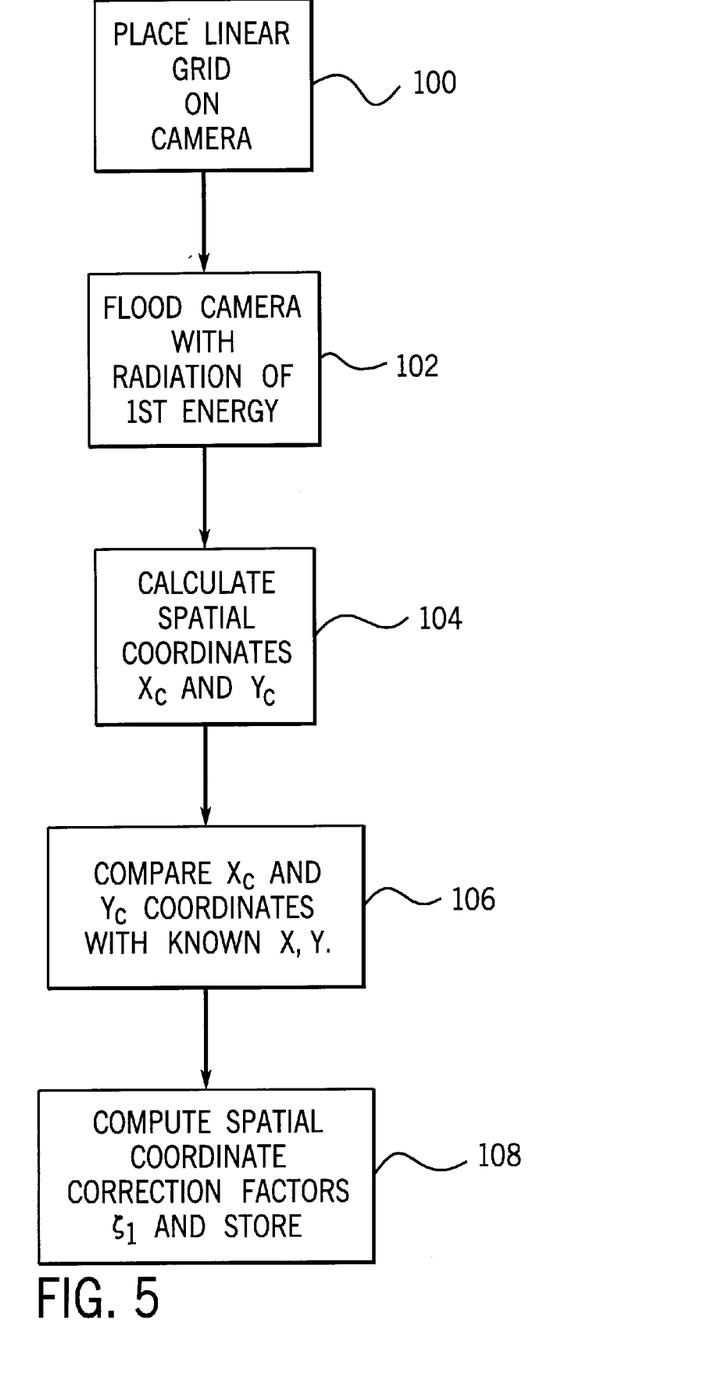
FIG. 5 is a flowchart illustrating a method by which a first correction factor set ζ1 is generated.

Referring now to FIG. 5, a preferred method for identifying a first correction factor set $\zeta 1$ is illustrated. Referring also to FIGS. 2, 3 and 4, to generate first correction factor set $\zeta 1$, at step 100 a linear grid of radiopaque material (e.g. a lead grid) is placed on camera 10 adjacent collimator 20. At step 102, camera 10 is flooded with radiation having an energy level equal to the energy level of photons emitted by a first radiopharmaceutical to be used for imaging. Radiation which subtends the grid is blocked while radiation which passes through grid portions and is perpendicular to length L impacts crystal 22 and generates light which is absorbed by PMTs 24. For each absorbed photon, each PMT 24 generates an intensity signal which is provided to processor 38 via bus 18. At step 104, processor 38 calculates spatial coordination Xc and Yc for each absorbed photon. At step 106 processor 38 compares calculated spatial coordinates Xc and Yc with known spatial coordinates X and Y which correspond to the known grid configuration and known grid position with respect to camera 10.

Next, at step 108, processors 38 computes spatial coordinate correction factors $\zeta 1$ which are required to compensate for any differences between calculated spatial coordinates Xc and Yc and known coordinates X and Y, respectively.

Figure 6:
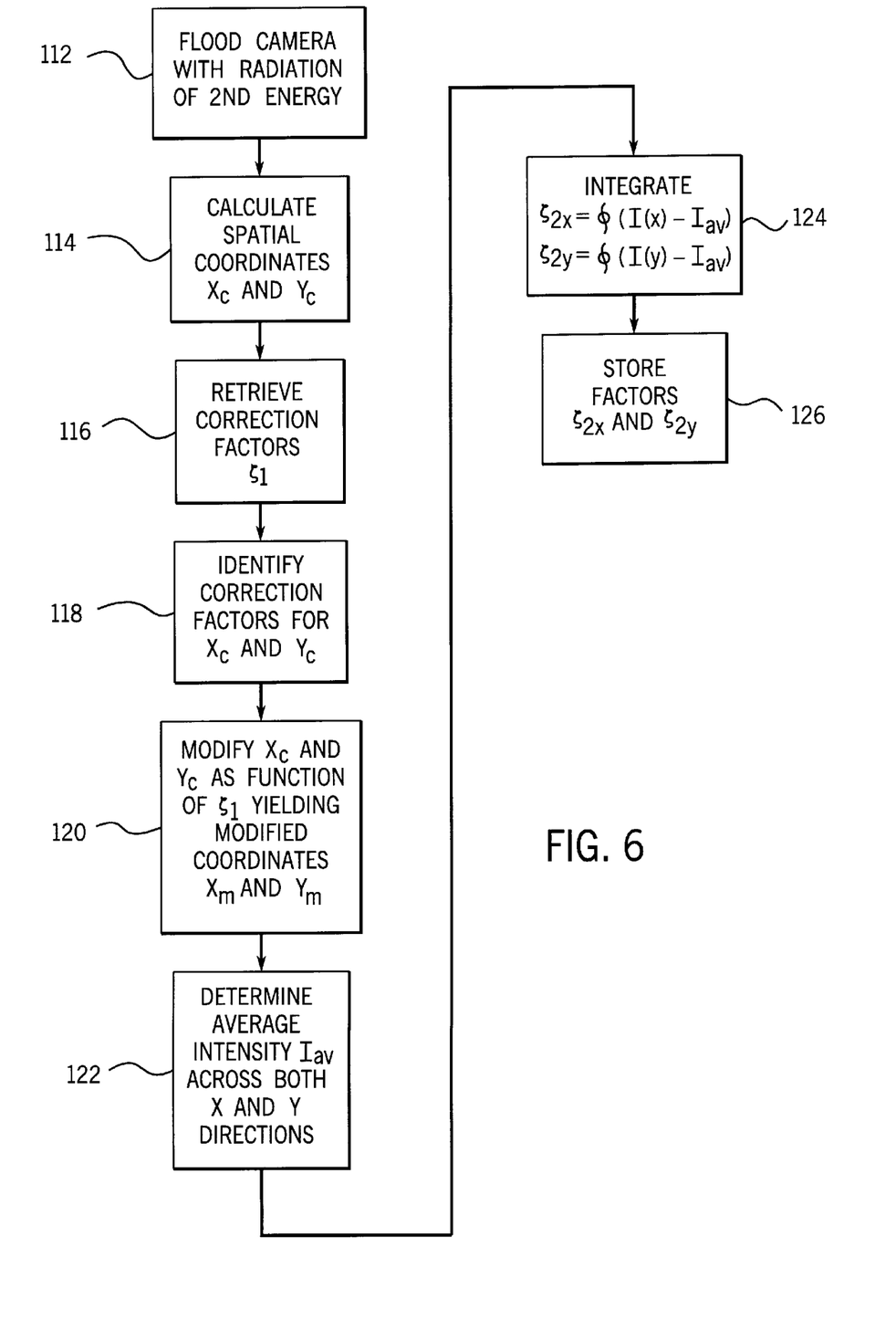
FIG. 6 is a flowchart illustrating how a second correction factor set ζ2 is generated.

Referring now to FIG. 6, the preferred method for identifying a second correction factor set $\zeta 2$ for correcting residual spatial distortions in calculated coordinates Xc and Yc for photons at the second energy level is illustrated. Referring also FIG. 2, 3 and 4, at step 112, camera 10 is flooded with radiation of the second energy level. This can be accomplished by providing a radiation point source at the second energy level a distance (i.e. 5 imaging fields away) from camera 10 so that uniform intensity subtends the camera 10. As known in the industry, the flood can be provided using an extrinsic sheet source also. As photons are detected by crystal 22, crystal 22 again generates light which is detected by PMTs 24, each PMT generating an intensity signal on a corresponding bus 18 which is received by processor 38. Processor 38 generates spatial coordinates Xc and Yc corresponding to photons at the second energy level at step 114. Next at step 116, processor 38 retrieves the first correction factor set $\zeta 1$. At step 118, processor 38 identifies correction factors $\zeta 1$ corresponding to coordinates Xc and Yc. At step 120 processor 38 modifies calculated spatial coordinates Xc and Yc generating adjusted coordinates Xm and Ym.

After calculated spatial coordinates Xc and Yc have been corrected using factors $\zeta 1$, some residual distortion will still remain and will follow the pattern of PMT rows and columns across array 32. That is, distortions along the X axis are independent of distortions along the Y axis and visa versa. This is because of the row and column arrangement of PMTs 24 in array 32. Therefore, residual distortion along the X axis can be derived from any horizontal profile through an image formed using modified coordinates Xm and Ym.

Similarly, residual distortion along the Y axis can be derived from any vertical profile through the image. The method of finding correction factors $\zeta 2$ for eliminating the residual distortion along both the X and Y axes is identical for each of the X and Y axes and therefore, in the interest of simplifying this explanation, the method will only be described in detail with respect to the Y axis.

Figure 7:
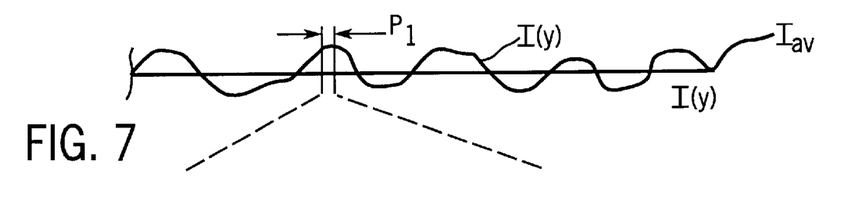
FIG. 7 is an exemplary one dimensional intensity waveform along the Y axis of FIG. 4.

Referring to FIGS. 1 and 7, an exemplary intensity profile along the Y axis is illustrated. The average intensity $I_{av}$ forms horizontal axis I(Y). The distortion of image pixels, some effectively becoming larger and others effectively becoming smaller than their true size, changes the apparent event count density within each pixel 200 and gives rise to a tube pattern which is hot where pixels 200 were shrunk and cold where pixels 200 were increased in size. For example, in FIG. 7, a pixel $P_1$ is indicated. Intensity across pixel $P_1$ is illustrated in more detail in FIG. 8. For pixel $P_1$, because the intensity in that pixel is greater than average intensity $I_{av}$, the intensity for pixel $P_1$ is relatively hot.

Because the intensity as a function of position Y is I(Y) and the average intensity of any pixel within the image is $I_{av}$, then the correction factor $\zeta 2$ for an individual pixel is given by the integral of the distortion across the pixel along the Y axis. Mathematically, the correction factor $\zeta 2$ along the Y axis can be represented by the equation:

$$\zeta_{2Y}\int=(I(Y)-I_{av})dy \qquad \text{Eq. 1}$$

Similarly, the correction factor along the X axis can be represented by equation:

$$\zeta_{2x}\int=(I(x)-I_{av})dx \qquad \text{Eq. 2}$$

where I(x) is the intensity as a function of position along the X axis.

Referring again to FIG. 6 and also to FIG. 1, to implement Equations 1 and 2, at step 122, processor 38 determines the average intensity $I_{av}$ of all pixels 200 in image array 202 across the X and Y directions. Next, at step 124, processor 38 solves Equation 1 for each pixel 200 along a vertical profile and solves Equation 2 for each pixel 200 along a horizontal profile thereby generating correction factors $\zeta 2X$ and $\zeta 2Y$ which comprise second correction factor set $\zeta 2$. At step 126 processor 38 stores second factor set $\zeta 2$.

Figure 8:
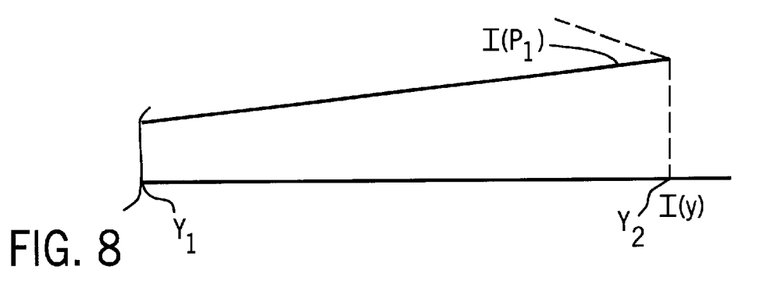
FIG. 8 is an enlarged view of a portion of the wave form of FIG. 7.
Figure 9:
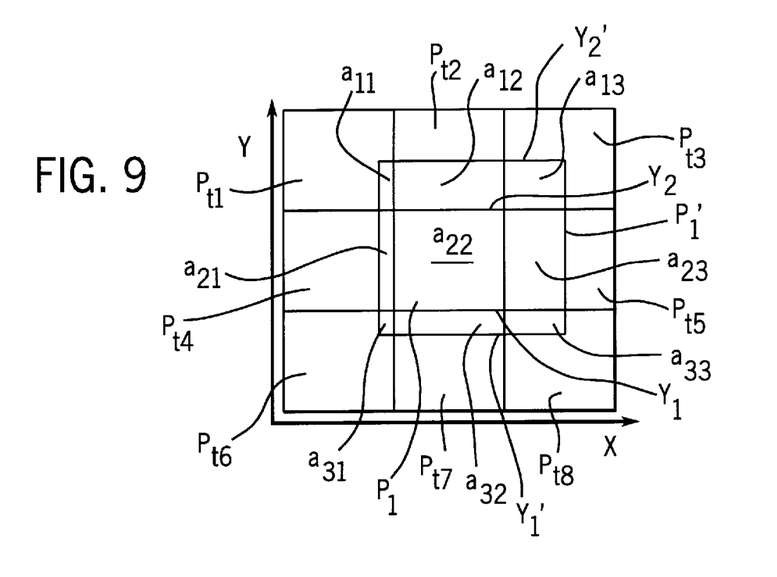
FIG. 9 is a schematic view of exemplary detector pixels.

The task of applying the second correction factor set $\zeta 2$ to correct for residual distortion in the adjusted event coordinates becomes a simple calculation of relative areas of an original pixel which are mapped into adjacent target pixels. For example, referring to FIGS. 1 and 9, pixel $P_1$ and surrounding target pixels $P_{T1}$ through $P_{T8}$ are illustrated. Referring also to FIGS. 7 and 8, because the intensity of exemplary pixel $P_1$ is greater than the average intensity $I_{av}$ (i.e. pixel $P_1$ is too hot), pixel $P_1$ effectively has to be enlarged to correct for errors. Thus, as in FIG. 9, pixel $P_1$ is increased in size so that it is the size of pixel $P'_1$ as illustrated. Note that pixel $P'_1$ is asymmetrically increased in size. This is because the intensity across pixel $P_1$ is not uniform across either the X or Y axes. Referring to FIG. 8, the intensity at a first end $Y_1$ is less than the intensity at a second end $Y_2$. Therefore, while the size of pixel $P_1$ must be increased at both ends $Y_1$ and $Y_2$, size has to be increased to a greater extent at end $Y_2$. In FIG. 9, edge $Y_1$ is pushed out to edge $Y'_1$ whereas edge $Y_2$ is pushed out a relatively greater distance to edge $Y'_2$. A similar process occurs along the X axis.

Event counts in original pixel $P_1$ can be mapped into new undistorted pixel $P'_1$ by taking the appropriate fraction of event counts in the original pixel and mapping that fraction of event counts into adjacent target pixels $P_{T1}$ through $P_{T8}$. To this end, sub areas $a_{11}$, $a_{12}$, $a_{13}$, $a_{21}$, $a_{22}$, $a_{23}$, $a_{31}$, $a_{32}$ and $a_{33}$ of pixel $P'_1$ are identified and the total area A of pixel $P'_1$ is identified. Then, each of areas $a_{11}$ through $a_{33}$ is divided by total area A to identify the fraction of total area A which lies in each of target pixels $P_{T1}$ through $P_{T8}$ and original pixel $P_1$. Next, assuming an original event count within original pixel $P_1$ is N, the correct number of event counts to be mapped into each of pixels $P_{T1}$ through $P_{T8}$ and $P_1$ can be identified by solving the following equation:

$$P_z = \left(\frac{a_{xy}}{A}\right)(N) \qquad \text{Eq. 3}$$

Where z is either $T_1$, $T_2$, $T_3$, $T_4$, $T_5$, $T_6$, $T_7$ or $T_8$ or 1. For example, if original event count N is 1,000 and area $a_{12}$ is 8% of area A, 80 events would be mapped into pixel $P_{T2}$.

D. Operation

Figure 10:
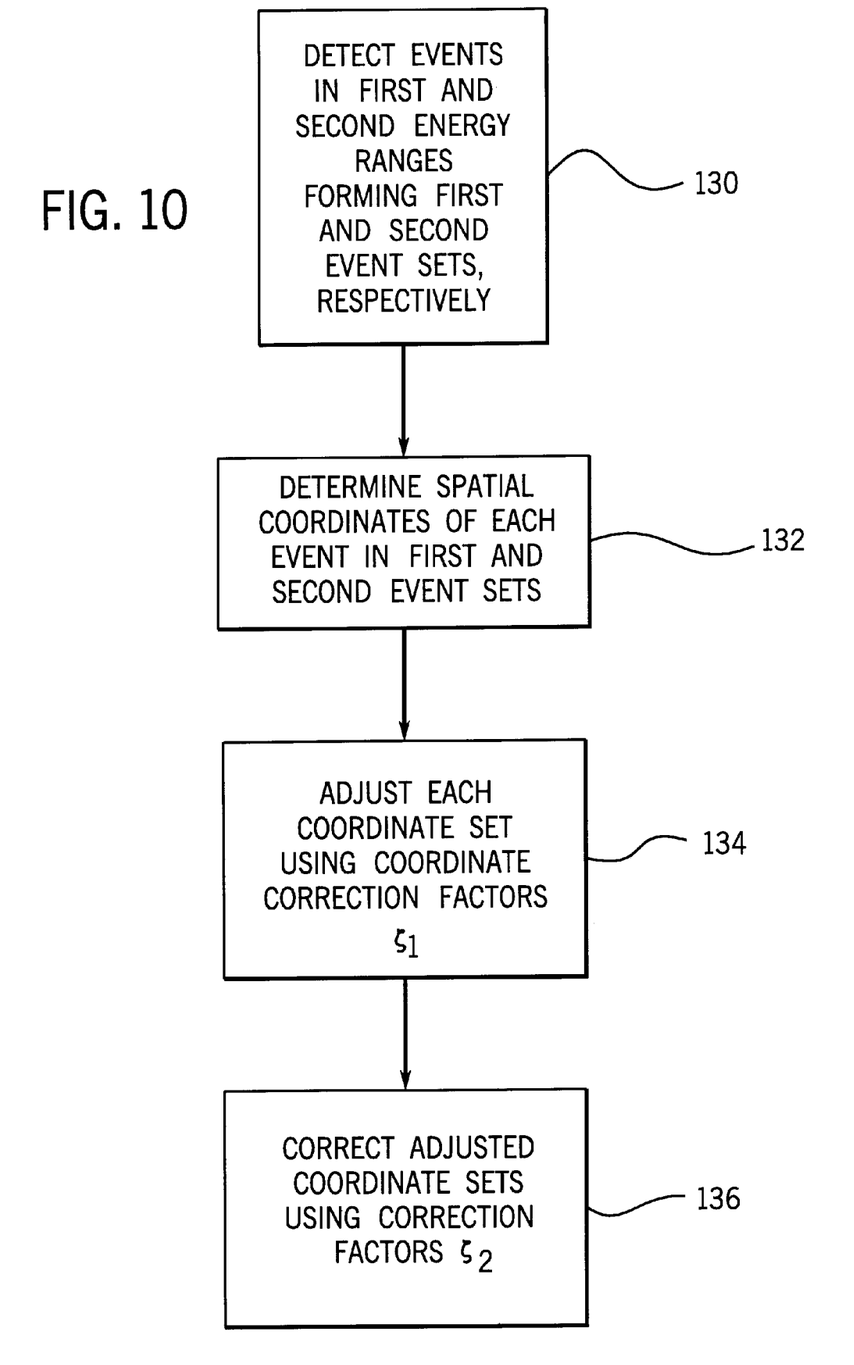
FIG. 10 is a flowchart illustrating a preferred invented method.

Referring now to FIG. 10, a preferred method for correcting coordinate spatial distortion corresponding to photons at first and second disparate energy levels is illustrated. Referring also to FIGS. 2, 3 and 4, when photons at first and second energy levels are directed at camera 10 deriving a data acquisition procedure, each photon which impacts crystal 22 emits a quantum of light which is directed at PMTs 24. PMTs 24 absorb the light and generate intensity signals as a function of photon energy level. Assuming the first photon energy level is less than the second photon energy level, intensity signals corresponding to an event at the first energy level have a combined magnitude which is less than the combined magnitude of intensity signals corresponding to an event at the second energy level. At step 130, processor 38 first detects events in the first and second energy ranges forming first and second events sets, respectively. Next, at step 132, processor 38 determines the spatial coordinates Xc and Yc of each event in the first and second event sets.

Continuing, at step 134, processor 38 adjusts each coordinate set Xc and Yc using coordinate correction factor set ζ1. This adjusting step yields a first corrected coordinate set corresponding to each event having an energy within the first range and an adjusted coordinate set corresponding to each event having an energy within the second range. The first corrected coordinate set and adjusted set are stored. After acquisition at step 136, processor 38 corrects each adjusted coordinate set with correction factors ζ2X and ζ2Y thereby eliminating spatial coordinate distortion in each adjusted coordinate set and yielding a second corrected coordinate set, corresponding to each event at the second energy level. The first and second corrected coordinate sets are then used to generate first and second images, respectively.

It should be understood that the methods and apparatuses described above are only exemplary and do not limit the scope of the invention, and that various modifications could be made by those skilled in the art that would fall under the scope of the invention. For example, while the present invention is described as one wherein a first correction factor set is applied during acquisition as second correction factor set is applied post acquisition, clearly, the invention is meant to cover systems wherein both the first and second correction factor sets are either applied during acquisition or, in the alternative, are applied post acquisition. In addition, while the invention is described as one wherein a first energy level is less than a second energy level, clearly, the first energy level could have a greater value than the second energy level.

Figure 11:
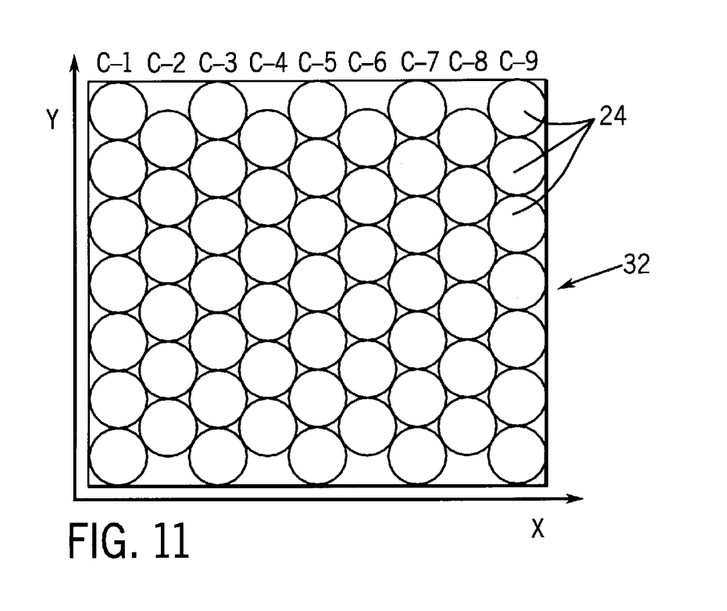
FIG. 11 is a view similar to FIG. 3, albeit with a different PMT arrangement.

Moreover, while one method for generating a second set of correction factors has been described, clearly, other methods for generating the second set of correction factors could be used. For example, referring to FIG. 11, instead of having distinct rows and columns of PMTs 24, PMTs 24 might be arranged to form an interleaved array 32. In this case, X and Y spatial distortions are not independent of each other. Thus, instead of using a flood acquisition as described with reference to FIG. 8, a radiopaque grid of known dimensions and known position with respect to camera 10 can be used. Then, after the first set of correction factors has been applied, a second set could be applied.

To apprise the public of the scope of this invention, I make the following claims:

I claim:

1. A method for correcting spatial coordinates of detected radiation events computed by a scintillation camera wherein the camera detects first and second event sets including events having energies within first and second energy ranges, respectively, the camera distorting spatial coordinates corresponding to each of the first and second energy ranges differently, the method comprising the steps of:
   (a) determining a spatial coordinate set for each detected event in either the first or second event sets;
   (b) adjusting each coordinate set with a first predetermined set of correction factors calculated to eliminate spatial coordinate distortion of events in the first event set thereby generating first corrected coordinate sets corresponding to each event having an energy within the first range and adjusted coordinate sets corresponding to each event having an energy within the second range; and
   (c) correcting each adjusted coordinate set with a second predetermined set of correction factors calculated to eliminate spatial coordinate distortion in each adjusted coordinate set, each corrected adjusted coordinate set being a second corrected coordinate set.

2. The method of claim 1 wherein the steps (a) and (b) are performed during radiation acquisition and step (c) is performed post-acquisition.

3. The method of claim 1 wherein the first range includes energies which are less than energies included in the second range.

4. The method of claim 3 wherein the first range includes energies which are approximately 140 keV and the second range includes energies which are approximately 511 keV.

5. The method of claim 1 further including the steps of, prior to determining, identifying events having energies within the first energy range as the first event set and identifying events having energies within the second energy range as the second event set.

6. The method of claim 5 wherein the step of determining also includes the step of identifying first and second groups of spatial coordinate sets corresponding to events in the first and second event sets, respectively, and wherein the step of adjusting each coordinate set includes correcting each coordinate set in the first group to generate the first corrected coordinate sets and adjusting each coordinate set in the second group to generate the adjusted coordinate sets.

7. An apparatus for correcting spatial coordinates of detected radiation events computed by a scintillation camera wherein the camera detects first and second event sets including events having energies within first and second energy ranges, respectively, the camera distorting spatial coordinates corresponding to each of the first and second energy ranges differently, the apparatus comprising:
   a determiner for determining a spatial coordinate set for each detected event in either the first or second event sets;

an adjuster for adjusting each coordinate set with a first predetermined set of correction factors calculated to eliminate spatial coordinate distortion of events in the first event set thereby generating first corrected coordinate sets corresponding to each event having an energy within the first range and adjusted coordinate sets corresponding to each event having an energy within the second range; and a corrector for correcting each adjusted coordinate set with a second predetermined set of correction factors calculated to eliminate spatial coordinate distortion in each adjusted coordinate set, each corrected adjusted coordinate set being a second corrected coordinate set.

8. The apparatus of claim 7 wherein the adjuster and corrector are a single corrector and the single corrector adjusts each coordinate set during radiation acquisition.

9. The apparatus of claim 8 wherein the single corrector corrects each adjusted coordinate set post-acquisition.

* * * * *